US009924899B2

(12) United States Patent
Pracar et al.

(10) Patent No.: US 9,924,899 B2
(45) Date of Patent: Mar. 27, 2018

(54) INTELLIGENT PROGRESSION MONITORING, TRACKING, AND MANAGEMENT OF PARKINSON'S DISEASE

(71) Applicants: Alexis Pracar, Piedmont, CA (US); Shane Pracar, Piedmont, CA (US)

(72) Inventors: Alexis Pracar, Piedmont, CA (US); Shane Pracar, Piedmont, CA (US)

( * ) Notice: Subject to any disclaimer, the term of this patent is extended or adjusted under 35 U.S.C. 154(b) by 41 days.

(21) Appl. No.: 14/021,982

(22) Filed: Sep. 9, 2013

(65) Prior Publication Data
US 2015/0073310 A1 Mar. 12, 2015

(51) Int. Cl.
*A61B 5/11* (2006.01)
*A61B 5/00* (2006.01)

(52) U.S. Cl.
CPC .......... *A61B 5/4082* (2013.01); *A61B 5/1101* (2013.01); *A61B 5/4842* (2013.01); *A61B 5/4848* (2013.01); *A61B 5/681* (2013.01); *A61B 5/74* (2013.01); *A61B 5/0002* (2013.01); *A61B 5/7455* (2013.01)

(58) Field of Classification Search
CPC ......... A61B 5/4082; A61B 5/74; A61B 5/681; A61B 5/4848; A61B 5/1101; A61B 5/4842; A61B 5/7455; A61B 5/0002
USPC ........ 600/300, 301, 595; 128/897, 898, 920, 128/922–925
See application file for complete search history.

(56) References Cited

U.S. PATENT DOCUMENTS

| | | | | |
|---|---|---|---|---|
| 2005/0234309 A1* | 10/2005 | Klapper | ......................... | 600/300 |
| 2009/0048542 A1* | 2/2009 | Varadan et al. | .............. | 600/595 |
| 2009/0312817 A1* | 12/2009 | Hogle | .................. | A61B 5/0492 |
| | | | | 607/54 |
| 2010/0169409 A1* | 7/2010 | Fallon et al. | .................. | 709/203 |
| 2011/0098608 A1* | 4/2011 | Griffiths et al. | .............. | 600/595 |
| 2013/0028489 A1* | 1/2013 | Tracton et al. | ............... | 382/128 |
| 2014/0257047 A1* | 9/2014 | Sillay et al. | .................. | 600/301 |
| 2014/0257141 A1* | 9/2014 | Giuffrida et al. | ............. | 600/595 |

OTHER PUBLICATIONS

"Parkinson's Diagnosis Questions", The Michael J. Fox Foundation for Parkinson's Research, [Online]. Retrieved from the Internet: < https://www.michaeljfox.org/understanding-parkinsons/i-have-got-what.php >, Accessed on Aug. 1, 2013, 2013, 4 pgs.

(Continued)

*Primary Examiner* — David J McCrosky
(74) *Attorney, Agent, or Firm* — Kwan & Olynick LLP

(57) ABSTRACT

Various embodiments of the present invention describe mechanisms configured to monitor, track, and manage symptoms of Parkinson's disease (PD). According to particular exemplary embodiments, a system includes sensors configured to monitor motion exhibited by a user having symptoms of Parkinson's disease, a processor configured to determine whether the motion constitutes a tremor episode, and memory configured to maintain data associated with the tremor episode, a severity rating associated with the tremor episode, and medication intake information. In exemplary embodiments, the effectiveness of a user's medication intake can be determined based on data displayed regarding severity rating variations over time in relation to medication intake.

14 Claims, 5 Drawing Sheets

(56) References Cited

OTHER PUBLICATIONS

"Parkinson's Disease", Wikipedia, [Online]. Retrieved from the Internet: < http://en.wikipedia.org/wiki/Parkinson%27s_disease >, Accessed on Aug. 1, 2013, 20 pgs.

"Parkinson's Disease Overview", National Parkinson Foundation, [Online]. Retrieved from the Internet: < http://www.parkinson.org/parkinson-s-disease.aspx >, Accessed on Aug. 1, 2013, 2013, 1 pg.

* cited by examiner

INTELLIGENT PROGRESSION MONITORING, TRACKING, AND MANAGEMENT OF PARKINSON'S DISEASE

TECHNICAL FIELD

The present disclosure relates to intelligent progression monitoring, tracking, and management of Parkinson's disease.

DESCRIPTION OF RELATED ART

Parkinson's disease (PD) is a neurodegenerative brain disorder that occurs when dopamine-producing cells are damaged or die. Dopamine typically helps to relay messages between the region of the brain called the substantia nigra and other parts of the brain to control movements of the body. When 60-80% of dopamine-producing cells are lost due to PD, motor symptoms begin to appear.

Typical motor symptoms include tremor, slowness of movement, rigidity, and postural instability. Tremor can be characterized by cyclical motion with a frequency between about 4 and 6 Hz (cycles per second), and often a pill-rolling motion. Tremor is most prominent when an individual is at rest, and less prominent when the individual engages in voluntary movement or sleep. Slowness of movement (also called Bradykinesia) can manifest as difficulty in the process of movement, from planning movements to executing movements. Often Bradykinesia can be seen as difficulties with fine motor skills (sewing, writing, etc.). However, different motions can be affected differently, such as when a person has difficulty walking but does not find the same difficulty with swimming or riding a bike. Rigidity occurs when muscles contract continuously, causing stiffness and difficulty of motion. Postural instability occurs when an individual has difficulty with balance and has frequent falls. Other motor symptoms may occur such as shuffling of the feet and difficulties with speech and swallowing. Because of the occurrence of motor difficulties in many suffering from PD, PD is often characterized as a movement disorder.

The cause of PD for most individuals is unknown. However, research indicates that there may be a combination of genetic and environmental factors at play. At one end of a continuum, genetic factors are suspected to be the primary cause for a small group of people that had inherited a particular mutated gene. At the other end of the continuum, environmental factors are suspected to be the primary cause for a group of people who ingested a substance known as MPTP that had contaminated a batch of heroin that they had used. Most cases fall somewhere between these extremes. Increased risk factors have been associated with individuals exposed to certain pesticides, herbicides, insecticides, and heavy metals, and those with close genetic relation to someone with PD.

Although there is currently no cure for PD, various treatments can be used to ease the symptoms associated with PD. Treatments include medication, surgery (including deep brain stimulation), physical therapy, occupational therapy, speech therapy, and support groups. Medications are typically used in the early stages of the disease and can include Levodopa, dopamine agonists, and/or MAO-B inhibitors. Additional medications can be used to treat non-motor symptoms such as disorders of speech, cognition, mood, behavior, and thought, as well as sleep disturbances. Surgery may be an appropriate option for more advanced stages of PD and can include lesional surgery or deep brain stimulation.

Each of the therapies described above involve varying degrees of effectiveness for a particular individual at a particular stage of the disease. Furthermore, each therapy includes risks and side effects. Although close medical supervision of individuals with PD is needed to adjust the amounts, dosages, and types of treatments administered, such supervision can be limited for early and middle stage cases subject to outpatient care. In such cases, periodic evaluation and self-assessment may be relied upon to determine or adjust types and dosages of medications, and the effectiveness of various therapies. However, information obtained from periodic evaluations and self-assessments can be limited. Accordingly, it is desirable to provide improved mechanisms to gather data about the effectiveness of therapies for individuals with PD.

SUMMARY

Various embodiments of the present invention describe mechanisms configured to monitor, track, and manage symptoms of Parkinson's disease (PD). According to particular exemplary embodiments, a system includes sensors configured to monitor motion exhibited by a user having symptoms of Parkinson's disease, a processor configured to determine whether the motion constitutes a tremor episode, and memory configured to maintain data associated with the tremor episode, a severity rating associated with the tremor episode, and medication intake information. In exemplary embodiments, the effectiveness of a user's medication intake can be determined based on data displayed regarding severity rating variations over time in relation to medication intake.

BRIEF DESCRIPTION OF THE DRAWINGS

The disclosure may best be understood by reference to the following description taken in conjunction with the accompanying drawings, which illustrate particular embodiments of the present invention.

DETAILED DESCRIPTION

Figure 1:
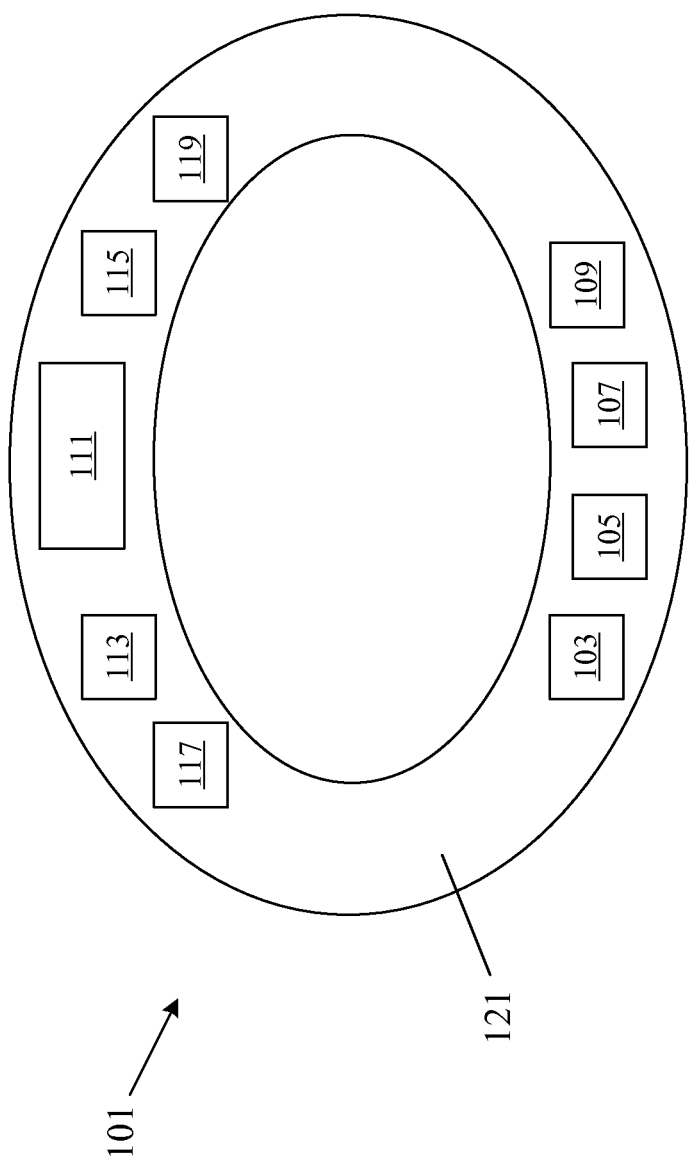
FIG. 1 illustrates one example of a system configured to monitor tremors of a user with Parkinson's disease.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Parkinson's disease (PD) is a neurodegenerative brain disorder that occurs when dopamine-producing cells are damaged or die. Because dopamine typically helps to relay messages between regions in the brain to control movements of the body, motor symptoms begin to appear when 60-80% of dopamine-producing cells are lost. Typical motor symptoms include tremor, slowness of movement, rigidity, and postural instability. Tremor can be characterized by cyclical motion with a frequency between about 4 and 6 Hz (cycles per second), and often a pill-rolling motion. Slowness of movement (also called Bradykinesia) can manifest as difficulty in the process of movement, from planning movements to executing movements. Rigidity occurs when muscles contract continuously, causing stiffness and difficulty of motion. Postural instability occurs when an individual has difficulty with balance and has frequent falls. Because of the occurrence of motor difficulties in many suffering from PD, PD is often characterized as a movement disorder.

Although there is currently no cure for PD, various treatments can be used to ease the symptoms associated with PD. Treatments include medication, surgery (including deep brain stimulation), physical therapy, occupational therapy, speech therapy, and support groups. Medications are typically used in the early stages of the disease and can include Levodopa, dopamine agonists, and/or MAO-B inhibitors. Additional medications can be used to treat non-motor symptoms such as disorders of speech, cognition, mood, behavior, and thought, as well as sleep disturbances. Surgery may be an appropriate option for more advanced stages of PD and can include lesional surgery or deep brain stimulation.

Each of the therapies described above involve varying degrees of effectiveness for a particular individual at a particular stage of the disease. Furthermore, each therapy includes risks and side effects. For instance, over time, Levodopa use can lead to motor complications called dyskinesias (involuntary movements) with fluctuations in the individual's response to medication.

Although close medical supervision of individuals with PD is needed to adjust the amounts, dosages, and types of treatments administered, such supervision can be limited for early and middle stage cases subject to outpatient care. In such cases, periodic evaluation and self-assessment may be relied upon to determine or adjust types and dosages of medications, and the effectiveness of various therapies. However, information obtained from periodic evaluations and self-assessments can be limited and inaccurate. For instance, self-monitoring can be inaccurate or sporadic.

Accordingly, the present invention provides improved mechanisms configured to monitor, track, and manage symptoms of Parkinson's disease (PD). Various embodiments of the present invention provide mechanisms for storing and displaying valuable and detailed information about the effectiveness of various medications taken by an individual with PD. By collecting data regarding the onset of PD symptoms in relation to the time and dosage of medications provided to an individual with PD, the present invention allows an individual with PD, their doctors, medical advisors, and family members, to access data in the form of graphs, charts, statistics, raw data, and the like, about the effectiveness of medications taken by the individual with PD. This detailed information can help doctors and medical advisors determine what types and doses of medications should be adjusted or changed. As a result, individuals with PD can benefit from more efficient treatment and less stress regarding monitoring their own symptoms.

FIG. 1 illustrates one example of a system configured to monitor tremors of a user with Parkinson's disease (PD). Tremors are a common motor symptom of PD that can be challenging both physically and socially. This motor symptom can be viewed as a repetitive, cyclical motion that can be detected by the present embodiment. As shown, the system 101 includes a band 121 with a memory 103, processor 105, and sensors 107. The sensors 107 can include one or more devices such as a gyroscope, accelerometer, gravimeter, and/or the like. The sensors 107 can be selected and configured to measure and detect cyclical motion associated with PD tremors. Processor 105 can be configured to compare the detected cyclical motion to a tremor episode threshold and determine whether the user is experiencing a tremor episode. For example, a tremor episode threshold can be established as having a frequency between about 4 and 6 Hz (cycles per second), and can include pill-rolling movements. In some embodiments, processor 105 can also be configured to determine a severity rating for a particular tremor episode.

In the present exemplary embodiment, memory 103 can store data associated with a tremor episode, a severity rating associated with the tremor episode, and medication intake information. According to various embodiments, memory 103 can also store data associated with severity level variations over time in relation to medication intake. Such data can be useful in determining the effectiveness medications taken by the user.

In some exemplary embodiments, the system 101 can include a network interface 109, which can include a plug, USB connection, BLUETOOTH(™), or the like. This network interface 109 can allow the system 101 to communicate and/or exchange data with other devices such as a smart phone, computer, etc. However, it should be noted that the system can be constructed to operate independently without a network interface 109 in some embodiments.

In the present exemplary embodiment, the system 101 can include an output interface 111, such as a touch screen or display. Some examples of displays that can be used with the present invention include a liquid crystal display (LCD), a flexible organic light emitting diode (OLED) display, a magnetic display, and a microelectromechanical systems (MEMS) display. The output interface 111 can present data such as the severity of a current tremor episode, latest medication intake information, tremor episode information over time, medication intake information over time, and/or effectiveness of medication taken over time. In some embodiments, the output interface 111 can also receive input, such as when a touch screen is used.

According to various exemplary embodiments, the band 121 can optionally include a speaker 113. The speaker 113 can present information such as audible reminders to take medications, audio versions of data displayed, etc. In addition, band 121 can optionally include a vibration mechanism 117. The vibration mechanism 117 can be used in various ways. For instance, vibrations can be used conjunction with an alarm or reminder to take medications. In another example, the vibration mechanism can be used as a reminder to do daily exercises, such as physical therapy, etc. In yet other examples, the vibration mechanism 117 can be programmed as an alarm to remind the user of scheduled activities or appointments.

Optionally, the band 101 can include a notification light 115. In some exemplary embodiments, this notification light can turn on, flash and/or blink as a reminder to take medication. Alternatively, this notification light can be used to display system conditions such as battery life, etc. This notification light may be a single color or multiple colors. In particular, the light could display a different color for different types of notifications, such as battery status, sleep mode, awake mode, etc. In other embodiments, the light could take the form of different shapes displayed for different types of notifications. For instance, awake mode could display a light in the shape of an open eye, sleep mode could display a light in the shape of a closed eye, and battery life can display a light in the shape of a battery, etc. The color of the shaped light might indicate whether the battery is fully charged (e.g. green), partially charged (e.g. yellow), or needs charge (e.g. red).

In some exemplary embodiments, the band 121 can include one or more buttons 119. These buttons can be used to control the output interface 111, speaker 113, notification light 115, vibration mechanism 117, or other parts of the system 101. For instance, it can be used to make a selection presented by the output interface 111, adjust the volume of the speaker 113, and/or activate the notification light 115.

According to the present embodiment, the band 121 can be designed as a bracelet, wristband, or other wearable device. Band 121 can be constructed from various materials, such as elastic, plastic, vinyl, rubber, etc. The material of the band can be rigid (like a hard plastic, etc.) or flexible (like silicone, rubber, etc.). According to various embodiments, the band 121 can be adjustable in size. For instance, band 101 can include a buckle, latch, or the like. In other examples, band 121 can overlap itself like a slap bracelet, so that it can be sized the user more easily. In another example, the band 121 can form a U-shape that can either leave an opening on one portion of the length or overlap itself to some extent. In yet other examples, band 121 can have a clasp that can adjustably attach to links, loops, or other openings on the band 121.

It should be noted that although the present embodiment shows a certain configuration of the components in band 121, the configuration is illustrative only and does not intend to limit the placement of various components. For instance, the location of speaker 113 and buttons 119 can be exchanged. Similarly, other components of the system 101 can be moved with respect to one another without departing from the scope of the present invention.

Figure 2:
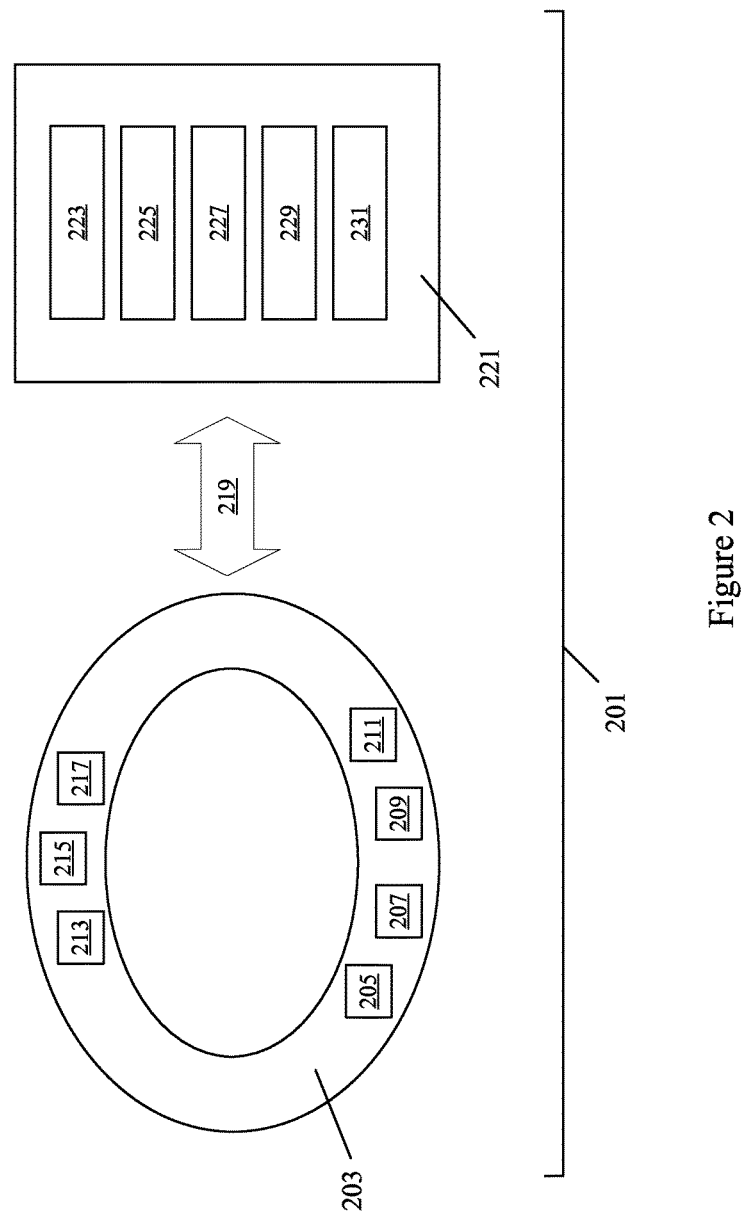
FIG. 2 illustrates another example of a system configured to monitor tremors of a user with Parkinson's disease.

FIG. 2 illustrates another example of a system configured to monitor tremors of a user with Parkinson's disease (PD). As shown, the system 201 includes a band 203 and remote device 221. According to the present embodiment, the band 203 can be designed as a bracelet, wristband, or other wearable device. Furthermore, remote device 221 can be a smart phone, computer, laptop, tablet, notebook, portable gaming device, or other interactive device.

In the present exemplary embodiment, band 203 includes sensors 205. The sensors 205 can include one or more devices such as a gyroscope, accelerometer, gravimeter, and/or the like. The sensors 205 can be selected and configured to measure and detect cyclical motion associated with PD tremors. In one example, motion constituting a tremor episode can have a frequency between about 4 and 6 Hz (cycles per second), and can include pill-rolling movements.

Optionally, the band 203 can include a notification light 213. In some exemplary embodiments, this notification light 213 can turn on, flash and/or blink as a reminder to take medication. Alternatively, this notification light can be used to display system conditions such as battery life, etc. This notification light 213 may display a single color or multiple colors. In particular, the light could display a different color for different types of notifications, such as battery status, sleep mode, awake mode, etc. In other embodiments, the light could take the form of different shapes displayed for different types of notifications. For instance, awake mode could display a light in the shape of an open eye, sleep mode could display a light in the shape of a closed eye, and battery life can display a light in the shape of a battery, etc. The color of the shaped light might indicate whether the battery is fully charged (e.g. green), partially charged (e.g. yellow), or needs charge (e.g. red).

According to various exemplary embodiments, band 203 can optionally include a vibration mechanism 215. The vibration mechanism 215 can be used in various ways. For instance, vibrations can be used conjunction with an alarm or reminder to take medications. In another example, the vibrations can be used as a reminder to do daily exercises, such as physical therapy, etc. In yet other examples, the vibration mechanism 215 can be programmed as an alarm to remind the user of scheduled activities or appointments.

In some exemplary embodiments, the band 203 can include one or more buttons 217. These buttons can be used to control notification light 213, interact with a remote device 221, or communicate with other parts of the band 203. For instance, it can be used to activate the notification light 213, such as to determine the current mode (e.g. awake, asleep, etc.) or to activate or switch to a certain mode (e.g. change from awake to asleep).

According to various exemplary embodiments, band 203 can be constructed from various materials, such as elastic, plastic, vinyl, rubber, etc. The material of the band can be rigid (like a hard plastic, etc.) or flexible (like silicone, rubber, etc.). According to various embodiments, the band 203 can be adjustable in size. For instance, band 203 can include a buckle, latch, or the like. In other examples, band 203 can overlap itself like a slap bracelet, so that it can be sized the user more easily. In another example, the band 203 can form a U-shape that can either leave an opening on one portion of the length or overlap itself to some extent. In yet other examples, band 203 can have a clasp that can adjustably attach to links, loops, or other openings on the band 203.

According to various exemplary embodiments, band 203 can optionally include simple memory 207 and/or simple processor 209. In some examples, simple memory 207 and/or simple processor 209 can be used to detect input from buttons 217. Additionally, simple memory 207 and/or simple processor 209 can be used to control notification light 213.

According to the present embodiment, band 203 includes a network interface 211, which can include a plug, USB connection, BLUETOOTH(™), or the like. This network interface 211 can allow the band 203 to communicate and/or exchange data with a remote device 221 such as a smart phone, computer, etc. Such communication can occur over a data connection 219 that can be wired, wireless, etc. depending on the chosen communication protocol.

In the present exemplary embodiment, remote device 221 includes an output interface 223, processor 225, memory 227, speaker 229, and network interface 231. Remote device 221 can be can be a smart phone, computer, laptop, tablet, notebook, portable gaming device, or other interactive device. In addition, remote device 221 can exchange, receive, and/or send communications and/or data with band 203 over data connection 219 using network interface 231.

In the present exemplary embodiment, processor 225 can be configured to compare cyclical motion of a user with PD to a tremor episode threshold to determine whether the user is experiencing a tremor episode. For example, a tremor episode can have a frequency between about 4 and 6 Hz (cycles per second), and can include pill-rolling movements. In some embodiments, processor 225 can also be configured to determine a severity rating for a particular tremor episode.

In the present exemplary embodiment, memory 227 can store data associated with a tremor episode, a severity rating associated with the tremor episode, and medication intake information. According to various embodiments, memory 227 can also store data associated with severity level variations over time in relation to medication intake. Such data can be useful in determining the effectiveness medications taken by the user.

According to the present embodiment, remote device 221 can include an output interface 223, such as a touch screen or display. Some examples of displays that can be used with the present invention include a liquid crystal display (LCD), flexible organic light emitting diode (OLED) display, magnetic display, or microelectromechanical systems (MEMS) display. The output interface 223 can present data such as the severity of a current tremor episode, latest medication intake information, tremor episode information over time, medication intake information over time, and/or effectiveness of medication taken over time. In some embodiments, the output interface 223 can also receive input, such as when a touch screen is used.

In the present embodiment, remote device 221 optionally includes speaker 229. The speaker 229 can present information such as audible reminders to take medications, audio versions of data displayed, etc. In some examples, speaker 229 can be used to sound an alarm to remind the user of scheduled activities or appointments. However, it should be noted that speaker 229 can be omitted in some embodiments.

It should be noted that although the present embodiment shows a certain configuration of the components in band 203 and remote device 221 of system 201, the configuration is illustrative only and does not intend to limit the placement of various components. For instance, the location of sensors 205 and vibration mechanism 215 can be exchanged within band 203. Furthermore, the placement of output interface 223 can be exchanged with speaker 229 within remote device 221. Similarly, other components of the system 201 can be moved with respect to one another without departing from the scope of the present invention.

Figure 3:
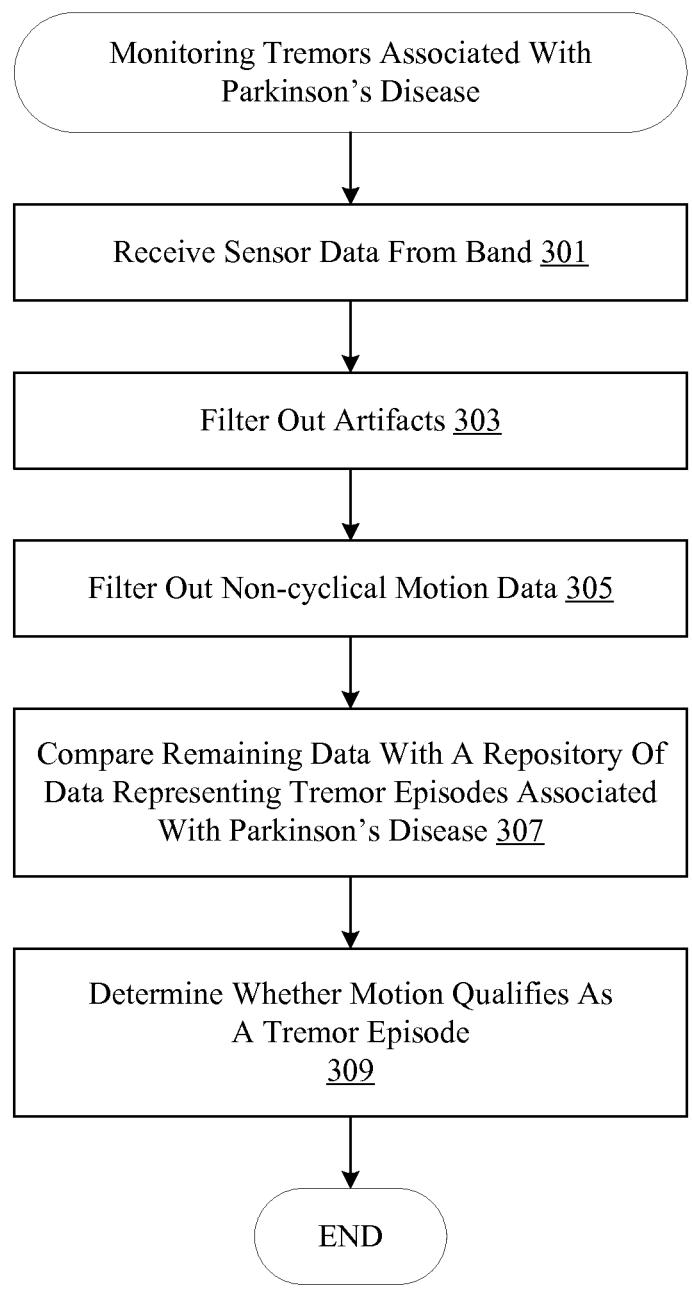
FIG. 3 illustrates an example of monitoring tremors of a user exhibiting symptoms of Parkinson's disease.

FIG. 3 illustrates an example of monitoring tremors of a user exhibiting symptoms of Parkinson's disease. Specifically, a user wears a band such as one described with regard to FIGS. 1 and 2 above. Sensors included in the band then detect the user's movements. At 301, sensor data regarding the user's movement is received from the band. According to various exemplary embodiments, the sensor data can be sent in a continuous stream or as packets of information at particular intervals of time. At 303, artifacts are filtered out from the data. Such artifacts can include data representing heartbeats, breathing, chewing, etc. that do not represent cyclical motion associated with PD. Next, at 305, non-cyclical motions are filtered out from the sensor data. Some examples of non-cyclical motions can include moving an arm to grab something, getting up from a chair, sitting down, etc.

The remaining sensor data is then compared with repository data corresponding to tremor episodes associated with PD at 307. The repository data can be stored in a database and can include characteristic waveforms corresponding to tremors. The waveforms and/or other repository data can be obtained from medical sources, empirical data, the user's own historical data, etc. One example of motion constituting a tremor episode has a frequency between about 4 and 6 Hz (cycles per second), and can include pill-rolling movements. In some exemplary embodiments, the repository data could be refined on an ongoing basis using data collected from the user. For instance, each time the system confirms that the user has had a tremor episode, waveforms and/or other information gathered during the tremor episode could be stored in the database.

Once the remaining sensor data is then compared with repository data corresponding to PD characteristic tremors, a determination is made at 309 whether the remaining sensor data qualifies as a tremor episode. For example, a detected cyclical motion can be compared to characteristic data for PD tremors. If the cyclical motion matches this characteristic data, then the system determines that the cyclical motion qualifies as a tremor episode. In contrast, if the cyclical motion does not match any of the characteristic data, then the system determines that the cyclical motion does not qualify as a tremor episode. Similarly, the cyclical motion can be compared to the repository data for various types of PD characteristic motions to determine if the cyclical motion detected exceeds a threshold determined to qualify as a tremor episode. In some embodiments, data about the detected tremor episode can be stored for reference. In addition, such data can be added to the database to be used for future detection of tremor episodes in some embodiments. Once a tremor episode is detected, then data associated with the tremor episode can be stored in a database and used to determine the effectiveness of medications taken, as described in more detail below with regard to FIG. 5.

Figure 4:
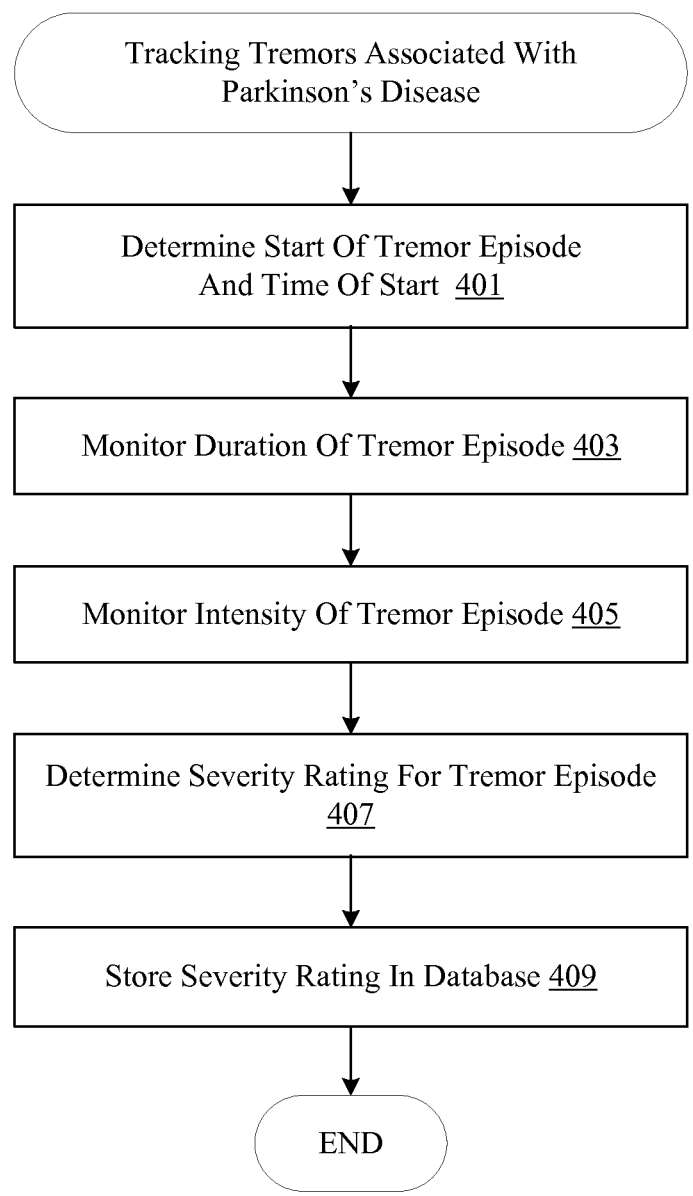
FIG. 4 illustrates an example of tracking tremors of a user exhibiting symptoms of Parkinson's disease.

FIG. 4 illustrates an example of tracking tremors of a user exhibiting symptoms of Parkinson's disease. According to this embodiment, the system detects a tremor episode and the start time of the tremor episode at 401. As described above with regard to FIG. 3, a tremor episode can be detected based on sensor input data that has been filtered and compared to information in a data repository that corresponds to characteristic PD tremor episodes.

Next, the duration of the tremor episode is monitored at 403. In some examples, the duration of the tremor episode can constitute the length of time the qualifying motions occur continuously. In other examples, the duration of the tremor episode can constitute the length of time a particular type of motion detected continues. For instance, if a pill-rolling motion of a certain frequency is detected, and the motion then evolves to a different frequency, duration of the motion can be broken down into two segments corresponding to the different frequencies.

In the present exemplary embodiment, the intensity of the tremor episode is monitored at 405. The intensity can be determined by the frequency and/or amplitude of the tremors detected. For instance, a motion with a frequency of 4 Hz may be considered to have a lower intensity than a motion with a frequency of 6 Hz. Similarly, the amplitude of the motion can be factored in to determine relative intensities of different detected motions.

According to the present embodiment, a severity rating is then determined for the tremor episode at 407. The severity rating can take into account the duration and intensity of the tremor episode. For instance, a rating of 10 could be assigned to the most severe tremor episodes, and a rating of 1 could be assigned to the least severe tremor episodes. More specifically, a rating of 10 could be assigned when the duration is long and the intensity is high. Furthermore, a rating of 1 could be assigned when the duration is short and the intensity is low. At 409, the severity rating can be stored in a database.

Figure 5:
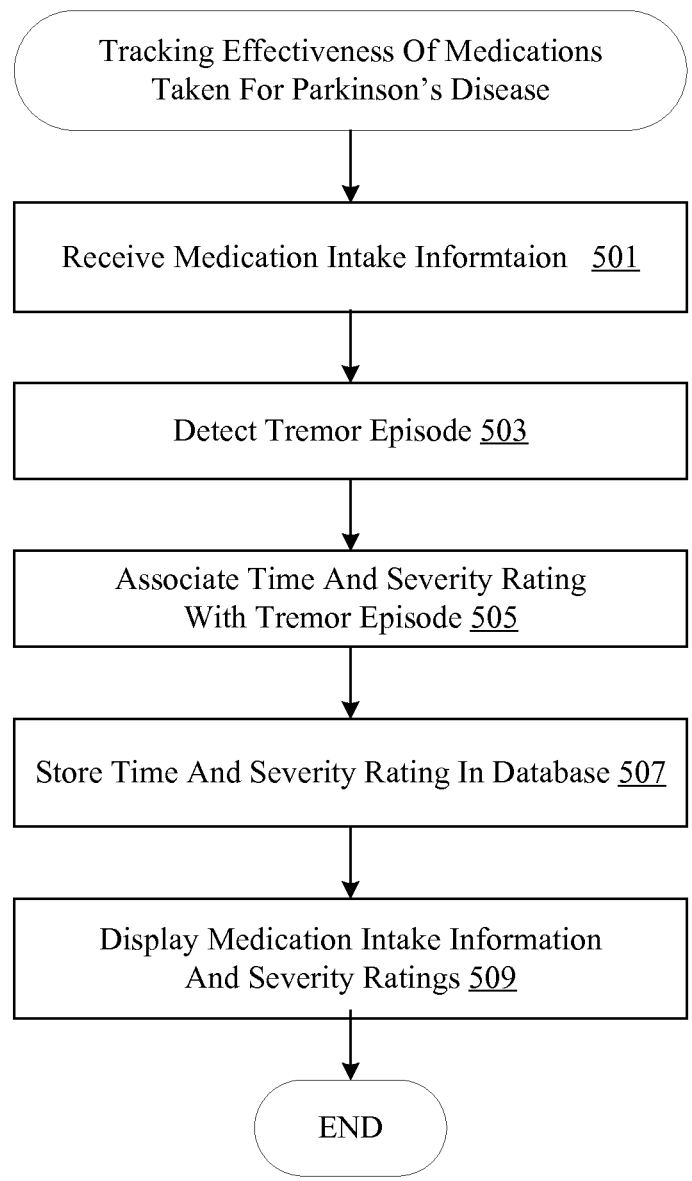
FIG. 5 illustrates an example of tracking the effectiveness of medications taken by an individual with Parkinson's disease.

FIG. 5 illustrates tracking the effectiveness of medications taken by a user with Parkinson's disease. By monitoring the effectiveness of a user's medication intake, the user and any doctors, family members, therapists, etc. can become aware of which treatments are most effective for the user. Furthermore, data about the effectiveness of particular medications and doses can be used to adjust the types of medications and doses recommended. In addition, the data can provide information about progression of the user's symptoms over time.

In the present exemplary embodiment, medication intake information is received at 501. Medication intake information can include medication type, dosage, and time taken. In some embodiments, particular therapies can be input for medication input information, such as when physical therapy and its effects are to be monitored. In such cases, the type, duration, and time of physical therapy can be input for medication input information. Next, at 503, a tremor episode is detected. As described above with regard to FIG. 3, a tremor episode can be detected based on sensor input data that has been filtered and compared to information in a data repository that corresponds to characteristic PD tremor episodes.

Once a tremor episode is detected, a time and severity rating can be associated with the tremor episode at 505. For instance, the time can be based on a 12-hour or 24-hour clock. In some examples, this can be based on a particular time zone or on Greenwich Meridian Time (GMT). A severity rating can be determined based on the duration and intensity of the tremor episode, as described in more detail above with regard to FIG. 4. Next, the time and severity rating is stored in a database at 507.

In the present embodiment, medication intake information and severity ratings can be displayed at 509. In particular, the medication intake information and severity ratings can be shown as a function of time. This information can be displayed in various forms. For instance, the information can be shown as a graph, chart, table, list, raw data, etc., depending on the preference of the viewer. In one example, a medication is taken at time A and two tremor episodes are detected at times B and C, respectively. If the tremor episodes were high intensity and began shortly after the medication was taken, a doctor could determine that either a higher dose or a different medication should be prescribed. If the tremor episodes were both low intensity and occurred long after the medication was taken, a doctor could determine that the user is beginning to form a tolerance to the medication such that the medication's effectiveness may wane before the next dosage. In another example, the data may indicate that fluctuations in the user's response to medication and appearance of motor complications called dyskinesias (involuntary movements) suggest side effects of extended Levodopa use. By evaluating when the tremor episodes occurred and how severe they were in relation to the user's mediation intake, a doctor could determine the effectiveness of a medication taken and adjust the prescription accordingly.

By making data available to users and doctors regarding the relationship of medication intake and tremor episodes, PD can be tracked and treated more effectively and more efficiently. In particular, a user's symptoms can be more accurately tracked and medications can be more accurately adjusted to treat these symptoms. Furthermore, the data can be used to determine the progression of PD symptoms over time. For instance, a graph could show that over a two year span, the severity of tremors detected has remained about the same, but a dosage of Levodopa has increased steadily over the two years. This could be used to gauge the progression of the disease and anticipate further treatments as well. Accordingly, the data associated with severity rating variations over time in relation to medication intake can be used to determine the effectiveness of the medication intake for a user.

While the invention has been particularly shown and described with reference to specific embodiments thereof, it will be understood by those skilled in the art that changes in the form and details of the disclosed embodiments may be made without departing from the spirit or scope of the invention. It is therefore intended that the invention be interpreted to include all variations and equivalents that fall within the true spirit and scope of the present invention.

What is claimed is:

1. A system comprising:
   a plurality of sensors included in a wearable bracelet device configured to monitor motion exhibited by a user having symptoms of Parkinson's disease, the motion including cyclical motion;
   a processor connected to the plurality of sensors, the processor configured to:
   determine whether the motion constitutes a tremor episode, wherein determining whether the motion constitutes a tremor episode includes filtering out artifacts data and non-cyclical motion data from the data associated with the tremor episode produced by the plurality of sensors and comparing the detected cyclical motion to characteristic data for Parkinson's disease tremors, and
   monitor a duration of the tremor episode, wherein the duration is a length of time that is the sum of two time segments, a first time segment corresponding to a first motion having a first frequency and a second time segment corresponding to a second motion having a second frequency, wherein the first motion evolves to a second motion; and
   memory configured to maintain data associated with the tremor episode, a severity rating associated with the tremor episode, clock time of the tremor episode, the duration of the tremor episode, and medication intake information, wherein medication intake information and severity ratings are displayed on the wearable device as a function of time, wherein the characteristic data for Parkinson's disease tremors is updated with the data associated with the tremor episode and stored in the memory for referencing subsequent tremor episodes.

2. The system of claim 1, wherein the processor is further configured to determine the severity rating for the tremor episode.

3. The system of claim 1, wherein the memory is further configured to maintain data associated with severity level variations over time in relation to medication intake such that effectiveness of the medication intake can be determined.

4. The system of claim 1, wherein the severity rating is determined based on frequency and amplitude of the motion.

5. The system of claim 1, wherein the severity rating is determined based on duration of the tremor episode.

6. The system of claim 1, wherein medication intake information comprises type, time, and dosage information.

7. A method for determining effectiveness of medication intake comprising:

monitoring motion exhibited by a user having symptoms of Parkinson's disease by using a plurality of sensors included in a wearable bracelet device, the motion including cyclical motion;

determining whether the motion constitutes a tremor episode by using a processor connected to the plurality of sensors, wherein determining whether the motion constitutes a tremor episode includes filtering out artifacts data and non-cyclical motion data from data produced by the plurality of sensors and comparing the detected cyclical motion to characteristic data for Parkinson's disease tremors;

monitoring a duration of the tremor episode, wherein the duration is a length of time that is the sum of two time segments a first time segment corresponding to a first motion having a first frequency and a second time segment corresponding to a second motion having a second frequency, wherein the first motion evolves to the second motion;

maintaining in a memory data associated with the tremor episode, a severity rating associated with the tremor episode, clock time of the tremor episode, the duration of the tremor episode, and medication intake information, wherein medication intake information and severity ratings are displayed on the wearable device as a function of time; and updating the characteristic data for Parkinson's disease tremors with the data associated with the tremor episode in the memory for referencing subsequent tremor episodes.

8. The method of claim 7, wherein the processor is further configured to determine the severity rating for the tremor episode.

9. The method of claim 7, wherein the severity rating is determined based on frequency and amplitude of the motion.

10. The method of claim 7, wherein the severity rating is determined based on duration of the tremor episode.

11. The method of claim 7, wherein medication intake information comprises type, time, and dosage information.

12. An apparatus for measuring effectiveness of medication intake comprising:

means for monitoring motion exhibited by a user having symptoms of Parkinson's disease, the motion including cyclical motion;

means for determining whether the motion constitutes a tremor episode, wherein determining whether the motion constitutes a tremor episode includes filtering out artifacts data and non-cyclical motion data from sensor data produced by a plurality of sensors and comparing the detected cyclical motion to characteristic data for Parkinson's disease tremors;

means for monitoring a duration of the tremor episode, wherein the duration is a length of time that is the sum of two time segments, a first time segment corresponding to a first motion having a first frequency and a second time segment corresponding to a second motion having a second frequency, wherein the first motion evolves to the second motion;

means for maintaining data associated with the tremor episode, a severity rating associated with the tremor episode, clock time of the tremor episode, the duration of the tremor episode, and medication intake information, wherein medication intake information and severity ratings are displayed on a wearable device as a function of time; and means for updating the characteristic data for Parkinson's disease tremors with the data associated with the tremor episode in memory for referencing subsequent tremor episodes.

13. The apparatus of claim 12, wherein a severity rating for the tremor episode is determined.

14. The apparatus of claim 12, wherein the severity rating is determined based on frequency and amplitude of the motion.

* * * * *